US007019847B1

(12) United States Patent
Bearman et al.

(10) Patent No.: US 7,019,847 B1
(45) Date of Patent: Mar. 28, 2006

(54) RING-INTERFEROMETRIC SOL-GEL BIO-SENSOR

(75) Inventors: Gregory Bearman, Pasadena, CA (US); David Cohen, Monrovia, CA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 345 days.

(21) Appl. No.: 10/750,574

(22) Filed: Dec. 9, 2003

(51) Int. Cl.
  *G01B 9/02* (2006.01)
(52) U.S. Cl. .................. 356/517; 436/164; 436/172; 356/480; 356/477
(58) Field of Classification Search ................ 356/517, 356/480, 483, 477; 250/227.19, 227.27
See application file for complete search history.

(56) References Cited

U.S. PATENT DOCUMENTS

| | | | |
|---|---|---|---|
| 3,539,262 A | 11/1970 | Pryor | 356/107 |
| 3,885,874 A | 5/1975 | Haas et al. | 356/107 |
| 5,173,747 A * | 12/1992 | Boiarski et al. | 356/481 |
| 5,377,008 A | 12/1994 | Ridgway et al. | 356/361 |
| 5,663,790 A | 9/1997 | Ekstrom et al. | 356/128 |
| 6,218,194 B1 | 4/2001 | Lyndin et al. | 436/518 |
| 6,248,539 B1 | 6/2001 | Ghadiri et al. | 435/7.1 |
| 6,381,025 B1 | 4/2002 | Bornhop et al. | 356/517 |
| 6,485,905 B1 | 11/2002 | Hefti | 435/6 |
| 6,576,430 B1 | 6/2003 | Hsieh et al. | |
| 6,657,731 B1 * | 12/2003 | Tapalian et al. | 356/480 |

OTHER PUBLICATIONS

Lukosz W., et al., "Integrated optical chemical and direct biochemical sensors", *Sensors and Actuators*, vol. B, No. 29, 1995, pp. 37-50, Elsevier Science, South America.

Schult, Karsten, et al., "Disposable Optical Sensor Chip for Medical Diagnostics: New Ways in Bioanalysis", *Analytical Chemistry*, vol. 71, No. 23, Dec. 1, 1999, pp. 5430-5435, American Chemical Society, USA.

Weisser, M., et al., "Specific bio-recognition reactions observed with an integrated Mach-Zehnder interferometer", *Biosensors & Bioelectronics*, vol. 14, 1999, pp. 405-411, Elsevier Science, South America.

Yamanaka, Stacey A., et al., "Enzymatic Activity of Glucose Oxidase Encapsulated in Transparent Glass by the Sol-Gel Method", *Chem. Mater.*, vol. 4, No. 3, 1992, pp. 495-497, American Chemical Society, USA.

(Continued)

*Primary Examiner*—Gregory Toatley
*Assistant Examiner*—Marissa J Detschel
(74) *Attorney, Agent, or Firm*—Mark Homer (57) ABSTRACT

A biosensor embodying the invention includes a sensing volume having an array of pores sized for immobilizing a first biological entity tending to bind to a second biological entity in such a manner as to change an index of refraction of the sensing volume. The biosensor further includes a ring interferometer, one volumetric section of the ring interferometer being the sensing volume, a laser for supplying light to the ring interferometer, and a photodetector for receiving light from the interferometer.

31 Claims, 5 Drawing Sheets

OTHER PUBLICATIONS

Hunsperger, Robert G., "Integrated Optics: Theory and Technology", 1991, pp. 110-113, Springer-Verlag, New York.

Bakul, Dave C., et al., "Sol-Gel Encapsulation Methods for Bionsensors", *Analytical Chemistry*, vol. 66, No. 22, Nov. 15, 1994, pp. 1120A-1127A, American Chemical Society, USA.

Ligler, Frances S., et al., "Optical Biosensors: Present and Future", 2002, pp. 427-456, Elsevier Science B.V., Netherlands.

Yamanaka, Stacey A., et al., "Enzymatic Activity of Oxalate Oxidase and Kinetic Measurements by Optical Methods in Transparent Sol-Gel Monoliths", *Journal of Sol-Gel Science and Technology*, vol. 7, 1996, pp. 117-121, Kluwer Academic Publishers, Netherlands.

* cited by examiner

RING-INTERFEROMETRIC SOL-GEL BIO-SENSOR

ORIGIN OF THE INVENTION

The invention described herein was made in the performance of work under NASA contract, and is subject to the provisions of Public Law 96-517 (35 U.S.C. § 202) in which the Contractor has elected not to retain title.

BACKGROUND OF THE INVENTION

A biosensor can be used to detect the presence of a specific antigen. These typically involve a sample of antibodies specific to the antigen of interest. There is a large class of biosensors that use immobilized antibodies on a surface as the sensing agent. The antibodies on the surface are identical and bind to a specific antigen, so that the sensor is specific to that particular antigen.

The antibody-antigen binding event must be detected. The traditional detection scheme in antibody sensors is fluorescence. In a typical sandwich assay, the immobilized antibody binds to the antigen; the system is then exposed to a fluorophore conjugated to the antibody, which then binds to the antigen. This tags the bound system upon exposure to light of a suitable wavelength.

The binding event also can be detected by the change in refractive index of the surface that occurs whenever antigens become bound to the antibodies on the surface. Such a biosensor is disclosed in U.S. Pat. No. 5,663,790, in which the bound antibodies are on a surface overlying an optical ring resonator. The change in refractive index shifts the resonant wavelength of the optical ring resonator. By sweeping the light frequency while observing the light intensity in the ring, the shift in resonant wavelength is observed, indicating a shift in refractive index and the corresponding event of the binding of the antigens to the antibodies.

One disadvantage of such a sensor is that the light source must have a variable wavelength that can be swept across a range. A related disadvantage is that the binding event can only be inferred after the light source wavelength has been swept across the range and the optical ring resonator response compared across the range. Another disadvantage is that the coupling between the change in refractive index in the sample and the detected optical output is limited because the sample is adjacent to and not within the optical ring interferometer. Finally, there appears to be no way of enhancing sensitivity of the sensor. The problem is that a very dilute antigen sample may not contain a sufficient population of antigens to bind to more than a small fraction of the bound antibodies, so that the change in refractive index may be so slight that the sensor cannot detect it.

What is needed is an optical sensor having an enhanced sensitivity capable of detecting extremely small changes in refractive index so as to be capable of sensing and measuring extremely weak or dilute antigen samples. Moreover, what is needed is a sensor that does not require expensive optical features such as a variable wavelength light source, and which does not require sweeping the light source wavelength across a range to make a measurement.

SUMMARY OF THE INVENTION

A biosensor embodying the invention includes a sensing volume having an array of pores sized for immobilizing a first biological entity tending to bind to a second biological entity in such a manner as to change an index of refraction of the sensing volume. The biosensor further includes a ring interferometer, one volumetric section of the ring interferometer being the sensing volume, a laser for supplying light to the ring interferometer, and a photodetector for receiving light from the interferometer.

The array of pores can be nanometer-sized pores. The array of pores may be Sol-Gel. The first biological entity may be an antibody and the second biological entity may be an antigen that binds to the antibody. Alternatively, the first biological entity may be a printed polymer and the second biological entity may be an antigen that binds to the printed polymer. Or, the first biological entity may be a first DNA or RNA strand and the second biological entity may be a second DNA or RNA strand that is complementary to the first strand.

DETAILED DESCRIPTION OF THE INVENTION

The problems described in the foregoing background discussion are solved by a biosensor in which the bound antibodies are immobilized in a nano-porous structure, such as Sol-Gel, that occupies a sensing volume within one arm or section of an optical ring interferometer. All the light traveling through that arm or section must pass through the bound antibody sensing volume, i.e., the nano-porous matrix, and thereby becomes a phase-shifted light beam due to the different index of refraction of the sensing volume. Another portion of the ring interferometer contains light that has not passed through the sensing volume, and interferes with the phase-shifted light beam. The degree of the interference is determined by the index of refraction of the sensing volume, which changes as antigens become bound to the immobilized antibodies in the sensing volume. The sensor is highly responsive in part because of the complete immersion of one portion of the ring interferometer in the Sol-Gel or nano-porous matrix. The sensor's sensitivity is greatly enhanced because the light makes multiple passes through the ring interferometer. The intensity of the interference pattern increases as the light circulates around the ring interferometer, thereby enhancing sensitivity of the sensor.

One advantage is that a variable wavelength light source is not required, and no frequency sweeping or comparison is required, so that the sensor is simple and its response is immediate.

Figure 1:
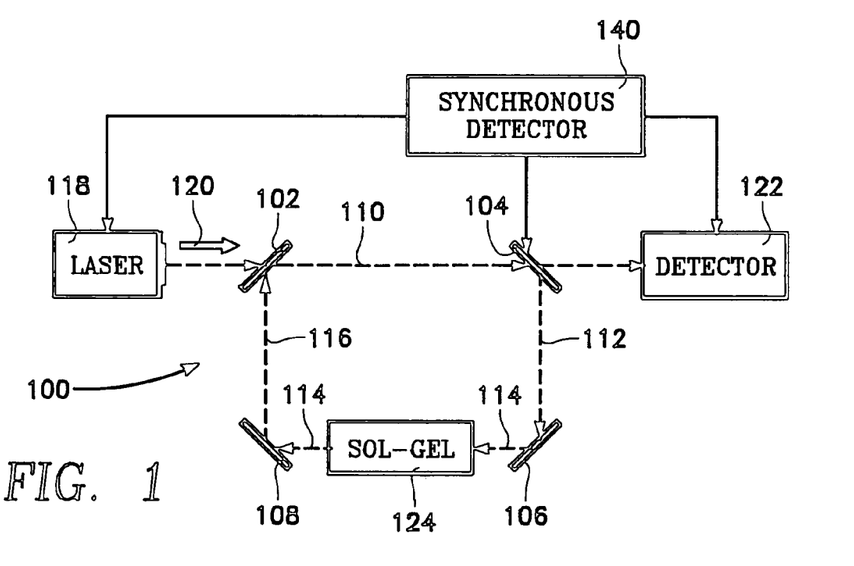
FIG. 1 is a schematic diagram of a first embodiment of the invention.

Referring to FIG. 1, an optical ring interferometer 100 includes four mirrors 102, 104, 106, 108 establishing a closed path consisting of optical paths 110, 112, 114, 116 of the ring interferometer 100. A laser 118 produces a light beam 120 that follows the optical paths 110–116 by reflection on the mirrors 102–108. The light beam 120 enters the optical path 110 through the backside of the mirror 102. The mirror 104 may be a beam splitter which transmits a portion of the light traveling along the optical path 110 to a detector 122 and reflects the remaining portion to the next optical path 112. A section of the optical path 114 is immersed in a sensing volume 124 consisting of a 3-dimensional array or matrix of nano-meter sized pores that are sized to attract and immobilize antibodies of a selected type. All of the light in the optical path 114 passes through the sensing volume 124. The array of nanometer-sized pores constituting the sensing volume 124 is best formed as a Sol-Gel structure of the type disclosed in Yamanaka et al., *J. Sol-Gel Sci. Technol.* 7, 117 (1996).

Figure 2:
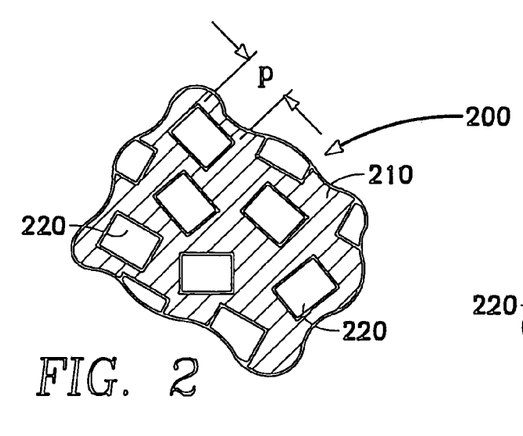
FIG. 2 is a partial cut-away cross-sectional view qualitatively depicting a Sol-Gel structure constituting the sensing volume in the embodiment of FIG. 1.
Figure 3:
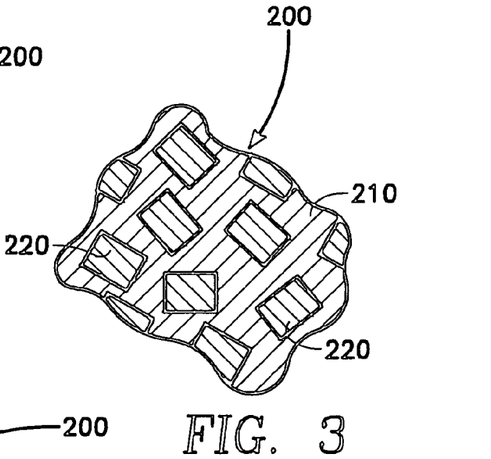
FIG. 3 is a view corresponding to FIG. 2 in which antibodies are held in the nanometer-size pores of the Sol-Gel structure.
Figure 4:
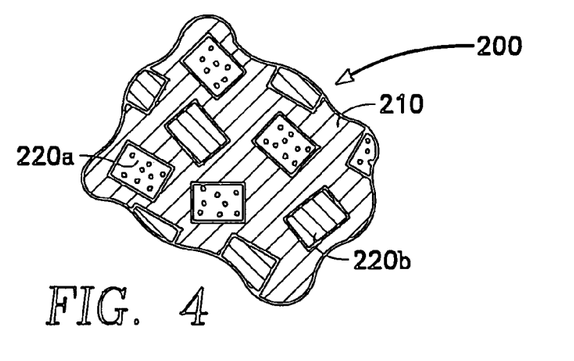
FIG. 4 is a view corresponding to FIG. 3 in which some of the antibodies have antigens bound to them, as symbolized by the shaded pores.

FIG. 2 is a qualitative illustration of a Sol-Gel structure 200 constituting the sensing volume 124, before its pores are filled with any material. In FIG. 2, the structure consists of a 3-dimensional base 210 having many 3-dimensional pores 220 formed within it. Each pore 220 has an average pore size P. The sol-gel precursor is a liquid that can be poured into the structure, the evaporation of the liquid leaving the sol-gel structure. Reference is made to a periodical dedicated to this technology, the *Journal of Sol-gel Science Technology*. The pore size P is chosen to correspond to the size of the antibody to be immobilized in each pore. This size ranges between a few nanometers and several hundred nanometers, depending upon the size of the particular antibody. The chosen antibody is one that binds to the antigen targeted by the sensor. In accordance with current practice, the base 210 can be formed of a material such as a silicon-based compound which is essentially inert with respect to biological materials such as antibodies and antigens, for example. The pore size P of the Sol-Gel is selected to attract and bind individual antibodies of a particular type within the pores, so that P is about the size of or somewhat larger than the selected antibody type, in accordance with conventional practice. FIG. 3 illustrates the Sol-Gel structure of FIG. 2 in which antibodies of a selected type have been immobilized in each pore 220. The selected antibody type determines the type of antigen targeted by the sensor. FIG. 4 illustrates the Sol-Gel structure of FIG. 2 in which the Sol-Gel structure of FIG. 3 has been immersed in or wetted with a fluid or analyte possibly containing the targeted antigen.

Depending upon the concentration of the targeted antigen in the analyte or fluid being tested, a certain fraction of the antibodies in the pores 220 receive and bind to antigens, as indicated by the dotted pores 220a. The remaining pores 220b contain immobilized antibodies but without antigens bound to them. Thus, FIG. 4 illustrates a case in which the Sol-Gel structure has been introduced to a relatively weak concentration of antigens so that only a portion of the immobilized antibodies in the Sol-Gel structure 200 receive and bind to antigens. The proportion of antigen-antibody bound pairs in the Sol-Gel structure 200 (i.e., their volume density) is a function of the concentration of antigens in the liquid or analyte introduced to the Sol-Gel structure 200, and other factors. An analyte having a very high concentration of the targeted antigen may saturate the Sol-Gel structure 200, so that all or nearly all of the immobilized antibodies may become bound to antigens. An analyte having a very weak concentration of the targeted antigen may cause antibody-antigen binding by only a small proportion of the immobilized antibodies.

The analyte may be introduced to the Sol-Gel structure 200 by flowing a liquid form of the analyte over the Sol-Gel structure 200. The analyte may either be the liquid itself or may be contained in the liquid. Unbound analyte is washed out of the Sol-Gel structure 200, leaving only the immobilized antibodies in the Sol-Gel structure 200 and any antigens from the analyte that became bound to the immobilized antibodies.

Binding of antigens to the immobilized antibodies in the Sol-Gel structure 200 changes the refractive index of the Sol-Gel structure 200 that constitutes the sensing volume 124. The density of antigen-antibody bound pairs in the Sol-Gel structure 200 determines the resulting change in refractive index. The magnitude of the change in refractive index resulting from the introduction of the analyte to the Sol-Gel structure is a measure of the concentration of the antigens in the analyte. The sensor therefore provides two pieces of information: (a) a detectable change in refractive index indicates the presence of the targeted antigen type in the analyte, while (b) the magnitude of the change in refractive index is indicative of the concentration of the targeted antigen in the analyte.

Referring to FIG. 1, an "unshifted" light beam 120 from the laser 118 travels through the mirror 102 to the optical path 110 and is transmitted by the beam splitter mirror 104 to the detector 122. A phase-shifted light beam consists of the portion of the light from the optical path 110 that is reflected by the beam splitter mirror 104 to the path 112, so that it travels through the optical paths 114, 116 and 110 (in that order). This light beam is phase shifted by passing through the sensing volume 124 occupying one section of the optical path 114. Thus, the light path 110 has a light beam traveling toward the beam splitter mirror 104 consisting of both the unshifted light beam and the phase shifted light beam. A portion of all the light in the optical path 110 is transmitted by the beam splitter mirror 104 to the detector 122, so that both the phase shifted and unshifted light beams impinge on the detector 122. The phase shift imposed by the sensing volume 124 causes interference between the shifted and unshifted light beams, which affects the intensity of the light sensed by the detector 122. The length of the optical path 110 as well as the total length of the interferometer ring 110, 112, 114, 116 are preferably integral numbers of wavelengths of the laser 118.

Figure 5:
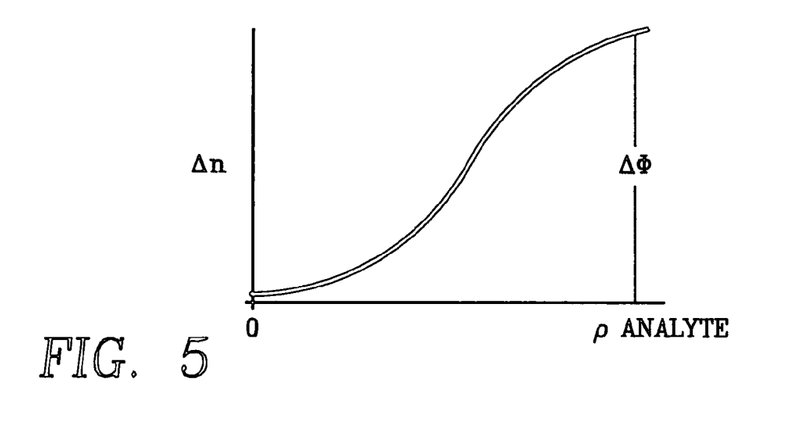
FIG. 5 is a graph illustrating the change in referactive index of the sensing volume in the embodiment of FIG. 1 as a function of analyte density (density of antibody-antigen bound pairs in the Sol-Gel structure of FIG. 4).
Figure 6:
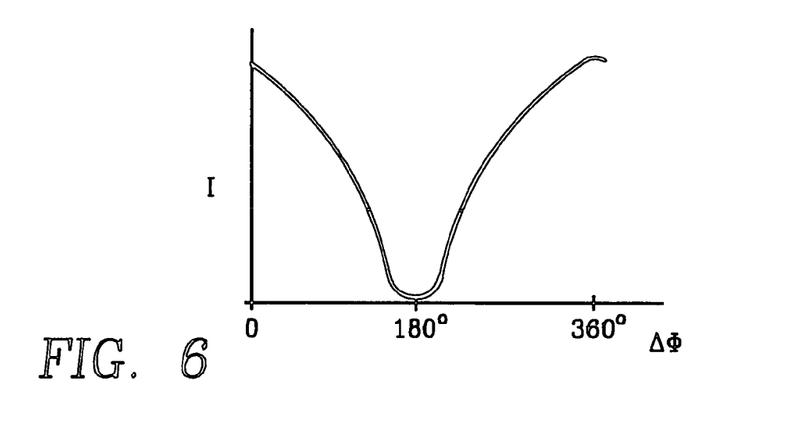
FIG. 6 is a graph illustrating the light output intensity of the ring interferometer of the embodiment of FIG. 1 as a function of the phase shift through the sensing volume.
Figure 7:
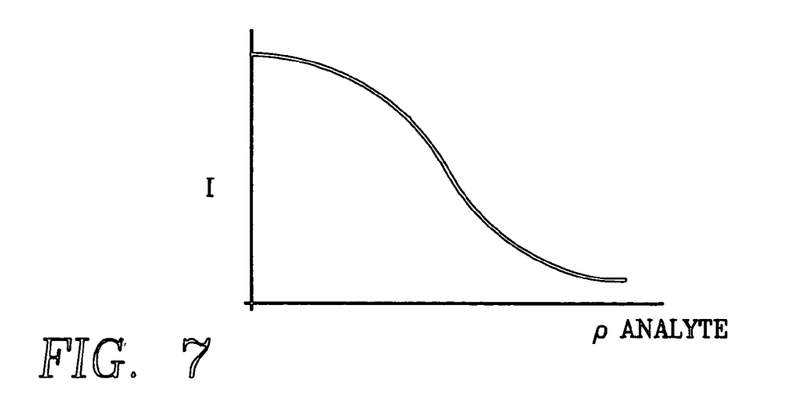
FIG. 7 is a graph illustrating the light output intensity of the ring interferometer as a function of analyte density.

Referring to graph of FIG. 5, the horizontal axis corresponds to the concentration, $\rho$, of the targeted antigen in the analyte, while the vertical axis corresponds to the change in refractive index, $\Delta n$ (left hand vertical axis) and, equivalently, to the phase shift, $\Delta \Phi$ (right hand vertical axis) of the light traveling in the optical path 114 through the sensing volume 124 containing the Sol-Gel structure 200. FIG. 5 qualitatively depicts the behavior in which stronger concentrations of the antigen in the analyte produce proportionately larger changes in refractive index and, hence, larger phase shifts. Such phase shifts change the interference between the shifted and unshifted light beams at the photodetector 122, producing corresponding changes in the light intensity at the photodetector 122. Referring to the graph of FIG. 6, the horizontal axis corresponds to the phase shift ΔΦ, while the vertical axis corresponds to the light intensity, I, sensed by the photodetector 122. As the phase shift between the "shifted" and "unshifted" light beams approaches 180 degrees, the light intensity at the photodetector approaches a minimum, as indicated by the graph of FIG. 6. The sensor may be constructed so that the phase shift is near zero in the absence of bound antibody-antigen pairs in the sensing volume 124 and approaches 180 degrees as the concentration of bound antibody-antigen pairs approaches saturation (100%). Two methods exist for modifying the index of refraction of the ring resonator in order to set its operating point. One method uses a polymer section of the waveguide which can have its index of refraction "written" by UV light, allowing device tuning during manufacture. Another method uses a small resistive heater on a portion of the waveguide to thermally tune the ring resonance point. In such implementations, the light intensity at the detector 122 decreases as the bound antibody-antigen concentration increases. This effect may be quantified by obtaining different samples of the photodetector output obtained using different concentrations of targeted antigen in different analytes. The results are illustrated in FIG. 7, in which the targeted antigen concentration ρ in the analyte is represented by the horizontal axis while the light intensity, I, corresponds to the vertical axis. In general, an increase in targeted antigen concentration in the analyte (over successive samples) causes a decrease in light intensity at the photodetector 122. However, other arrangements of the sensor may be made by the skilled worker that may reverse the behavior illustrated in FIG. 7. In either case, the change in measured intensity I at the photodetector may be employed as a measure of targeted antigen concentration p in the analyte.

Synchronous detection may be employed in the sensor of FIG. 1. For this purpose, a synchronous detection control circuit 140 may control the pulse width and repetition rate of the laser 118 while enabling the detector 122 in synchronism with the pulses of the laser 118. Alternatively, rather than pulsing the laser 118, the synchronous detection control circuit 140 can dither one of the mirrors (e.g., the mirror 104) to pulse the light propagation in the ring interferometer. The synchronous detection control circuit 140 would enable the detector 122 in synchronism with the dithering of the mirror so that the detector 122 is enabled with each pulse of light.

Figure 8:
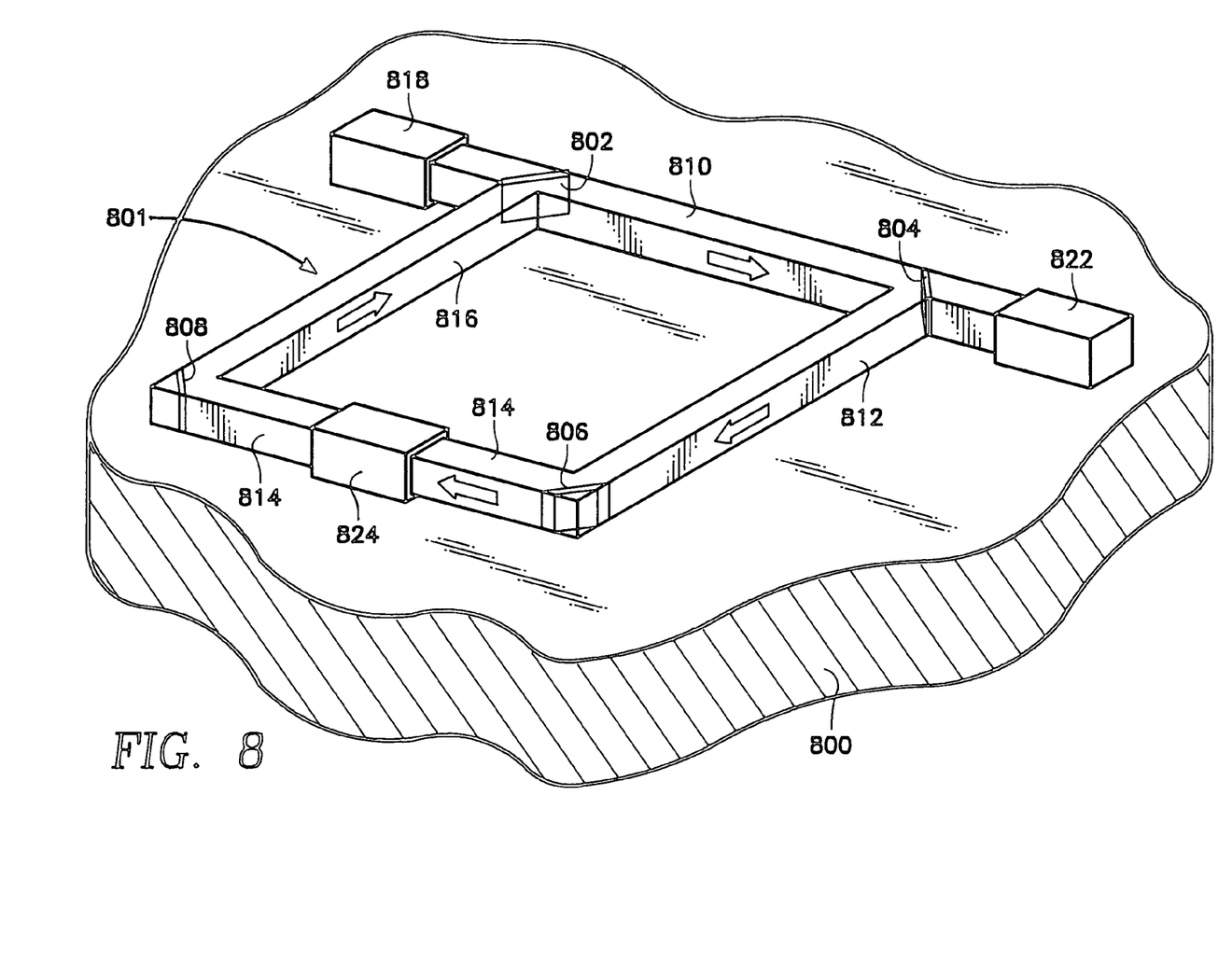
FIG. 8 is a perspective view of a second embodiment of the invention.

FIG. 8 illustrates an integrated implementation of the sensor of FIG. 1 implemented on a substrate 800. The substrate is formed of an optically transparent material such as glass or plastic or a semiconductor material or a ceramic. The optical paths 110, 112, 114, 116 of FIG. 1 are implemented in FIG. 8 as a closed waveguide 801 having connected sections 810, 812, 814, 816. The waveguide 801 is formed as a mesa or rib structure by etching the surface of the substrate 800 or by other methods well-known in the art. The cross-sectional height and width of the waveguide 801 may be selected by the skilled worker to support a single optical mode at the frequency of the laser 818. Mirrors 802, 804, 806, 808 are placed at each corner between successive waveguide sections 810, 812, 814, 816. A laser 818 is formed on the substrate 800 and feeds light into the waveguide 801 through the back of the mirror 802. A photodetector 822 is formed on the substrate 800 and receives light transmitted through the mirror 804. The mirror 804 performs the same function as the mirror 104 of FIG. 1, in that it transmits a portion of the light in the waveguide section 810 to the photodetector 822 while reflecting the remaining portion to the next waveguide section 812. A sensing volume 824 occupies a section of the waveguide 814 and consists of Sol-Gel structure 200 of FIGS. 2, 3 or 4. One advantage of the integrated sensor of FIG. 8 is that it can be highly compact, especially if the laser 818 is a semiconductor diode laser and the photodetector 822 is a semiconductor photodiode.

While the embodiments of FIGS. 1 and 8 employ a four-sided optical path as the ring interferometer, the number of sides can be any number ranging from three up to any practical number.

Figure 9:
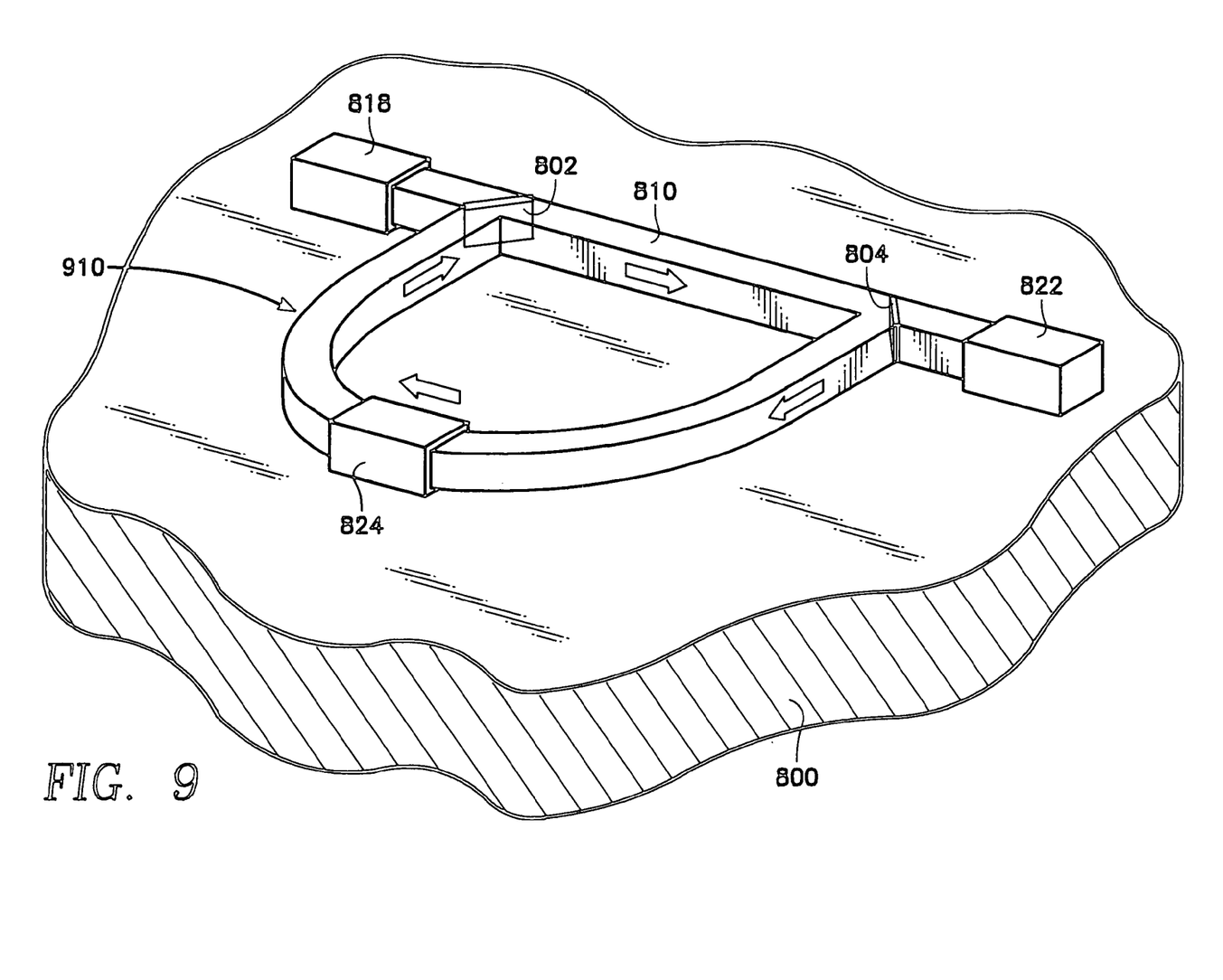
FIG. 9 is a perspective view of a third embodiment of the invention.

FIG. 9 illustrates a modification of the sensor of FIG. 8 in which the three waveguides sections 812, 814, 816 and the mirrors 806, 808 are replaced by a semicircular waveguide 910, a section of which is occupied by the sensing volume 824.

Figure 10:
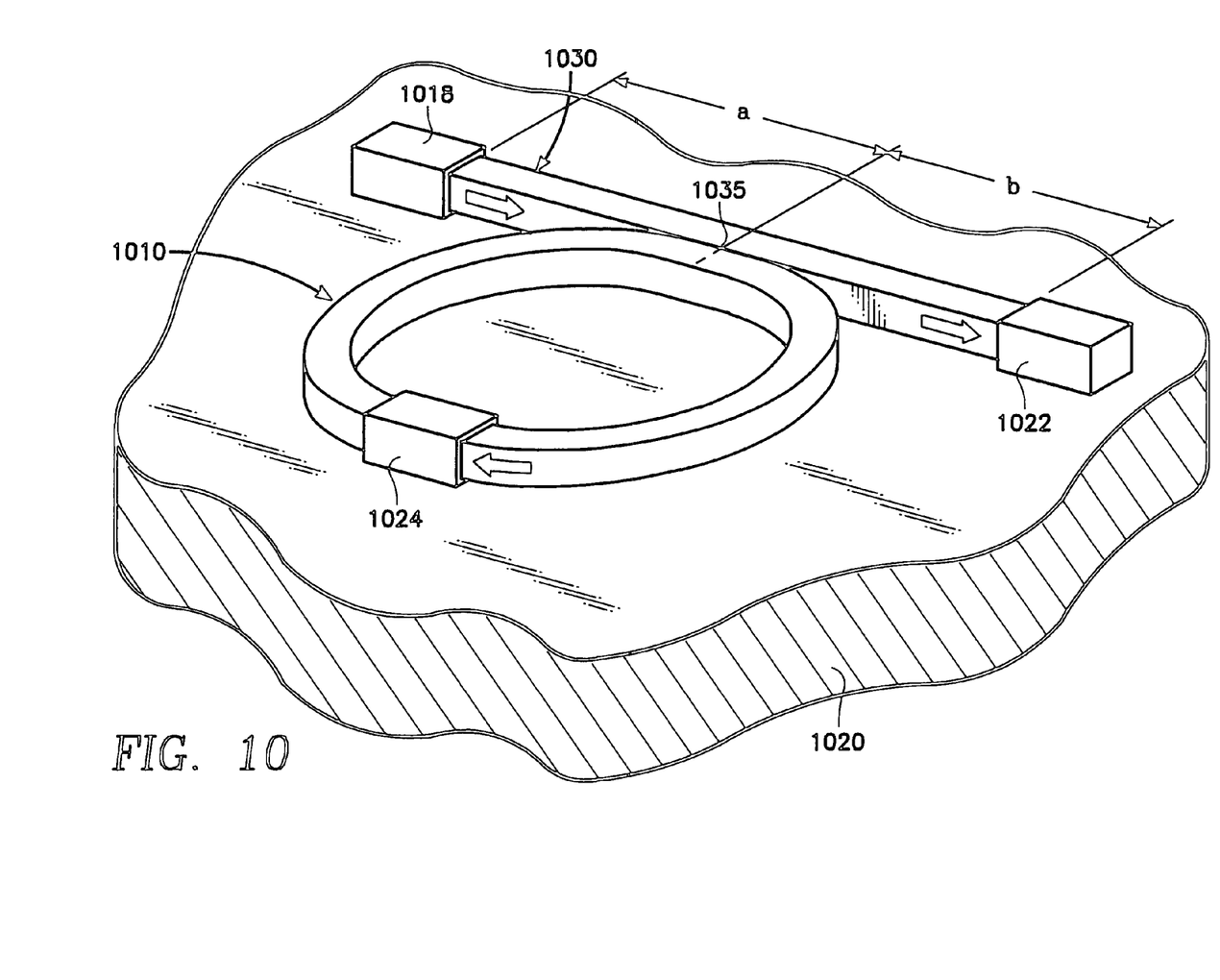
FIG. 10 is a perspective view of a fourth embodiment of the invention.

FIG. 10 illustrates an embodiment in which the ring interferometer is implemented using a full circular waveguide 1010 formed as a mesa structure on a substrate 1020. Light is supplied to the circular waveguide 1010 by evanescent coupling from a linear waveguide 1030 adjacent or tangent to the circular waveguide 1010 at a contact point 1035. The term "evanescent coupling" is defined in: Hunsperger, Robert M., *Integrated Optics: Theory and Technology*, 1991, pp. 110–113, Springer-Verlag, New York. As employed in this specification, the term "evanescent coupling" is the same as "optical tunneling" referred to in the foregoing publication. The linear waveguide 1030 has a laser 1018 at one end and a photodetector 1022 at the other end. The distance "a" between the laser 1018 and the contact point 1035, the distance "b" between the contact point 1035 and the photodetector 1022 and the pathlength of the circular waveguide are all integral multiples of the wavelength of the laser 1018. A sampling volume 1024 containing the Sol-Gel structure 200 of FIGS. 2, 3 or 4 occupies a section of the circular waveguide 1010. Light is coupled from the laser 1018 to the circular waveguide 1010 by evanescent coupling, and light is coupled from the circular waveguide to the photodetector by evanescent coupling between the circular and linear waveguides 1010, 1030 at the contact point 1035. Thus, the photodetector 1022 receives a first light beam directly from the laser 1018 as well as a second ("shifted") light beam that has passed through the sampling volume 1024. The second light beam is phase shifted by an amount depending upon the number of antigen-antibody bound pairs in the sensing volume. Thus, the light intensity sensed by the photodetector 1022 is a function of the interference between the two light beams in the same manner as described above with reference to the sensors of FIGS. 1 and 8.

While the sensor has been described with reference to implementations in which an antibody for the targeted antigen is immobilized in the Sol-Gel structure, artificial antibodies, i.e., printed polymers, could be substituted for the antibodies immobilized in the Sol-Gel. As another alternative, the sensor could be employed to sense or measure other biological binding events, such as, for example, binding between a pair of complementary DNA strands. In this case, the Sol-Gel porous structure would be sized to immobilize single DNA strands. An analyte possibly containing the complementary DNA strand would be introduced to the Sol-Gel. Complementary DNA strands would bind to the immobilized DNA strands, thereby changing the refractive index of the Sol-Gel. Thus, in general, the sensor detects binding between complementary biological entities, one of which is immobilized in the Sol-Gel and one of which is the targeted entity to be detected.

While the invention has been described in detail by specific reference to preferred embodiments, it is understood that variations and modifications thereof may be made without departing from the true spirit and scope of the invention.

What is claimed is:

1. A biosensor comprising:
a sensing volume comprising an array of pores sized for immobilizing within said pores a first biological entity tending to bind to a second biological entity in such a manner as to change an index of refraction of said sensing volume;
a ring interferometer, one volumetric section of said ring interferometer comprising said sensing volume;
a laser for supplying light to said ring interferometer;
a photodetector for receiving light from said interferometer.

2. The biosensor of claim 1 wherein said array of pores comprises nanometer-sized pores.

3. The biosensor of claim 1 wherein said array of pores comprises Sol-Gel.

4. The biosensor of claim 1 wherein said first biological entity comprises an antibody and said second biological entity comprises an antigen that binds to said antibody.

5. The biosensor of claim 1 wherein said first biological entity comprises a printed polymer and said second biological entity comprises an antigen that binds to said printed polymer.

6. The biosensor of claim 1 wherein said first biological entity comprises a first DNA or RNA strand and said second biological entity comprises a second DNA or RNA strand that is complementary to the first strand.

7. The biosensor of claim 1 wherein said ring interferometer comprises:
a first optical path between said laser and said photodetector;
a second optical path that includes said one volumetric section comprising said sensing volume, said second optical path comprising a closed recirculating optical path, said second optical path being coupled to said first optical path whereby said first optical path receives light from said laser unaffected by said sensing volume and light that has passed through said sensing volume.

8. The biosensor of claim 7 wherein said second optical path includes said first optical path.

9. The biosensor of claim 7 wherein said second optical path is separate from said first optical path and is coupled to said first optical path by evanescent coupling.

10. The biosensor of claim 1 further comprising a synchronous detection control circuit enabling said photodetector in synchronism with a burst mode transmission of light in said ring interferometer.

11. The biosensor of claim 7 wherein said first and second optical paths comprise respective waveguides.

12. The biosensor of claim 11 wherein said respective waveguides are formed on a monolithic substrate, said respective waveguides comprising mesa rib structures on said substrate.

13. The biosensor of claim 12 wherein said first optical path is along a straight line and said second optical path comprises a closed recirculating path.

14. The biosensor of claim 13 wherein said closed path comprises plural straight paths defining a polygonal shape.

15. The biosensor of claim 13 wherein said closed path lies along a circle.

16. A biosensor comprising:
a sensing volume comprising an array of pores sized for immobilizing within said pores a first biological entity tending to bind to a second biological entity in such a manner as to change an index of refraction of said sensing volume;
units of said first biological entity immobilized in respective ones of said pores;
a ring interferometer, one volumetric section of said ring interferometer comprising said sensing volume;
a laser for supplying light to said ring interferometer;
a photodetector for receiving light from said interferometer.

17. The biosensor of claim 16 wherein said array of pores comprises nanometer-sized pores.

18. The biosensor of claim 16 wherein said array of pores comprises Sol-Gel.

19. The biosensor of claim 16 wherein said first biological entity comprises an antibody and said second biological entity comprises an antigen that binds to said antibody.

20. The biosensor of claim 16 wherein said first biological entity comprises a printed polymer and said second biological entity comprises an antigen that binds to said printed polymer.

21. The biosensor of claim 16 wherein said first biological entity comprises a first DNA strand and said second biological entity comprises a second DNA strand that is complementary to said first DNA strand.

22. The biosensor of claim 16 wherein said ring interferometer comprises:
a first optical path between said laser and said photodetector;
a second optical path that includes said one volumetric section comprising said sensing volume, said second optical path comprising a closed recirculating optical path, said second optical path being coupled to said first optical path whereby said first optical path receives light from said laser unaffected by said sensing volume and light that has passed through said sensing volume.

23. The biosensor of claim 22 wherein said second optical path includes said first optical path.

24. The biosensor of claim 22 wherein said second optical path is separate from said first optical path and is coupled to said first optical path by evanescent coupling.

25. The biosensor of claim 16 further comprising a synchronous detection control circuit enabling said photodetector in synchronism with a burst mode transmission of light in said ring interferometer.

26. The biosensor of claim 22 wherein said first and second optical paths comprise respective waveguides.

27. The biosensor of claim 26 wherein said respective waveguides are formed on a monolithic substrate, said respective waveguides comprising mesa rib structures on said substrate.

28. The biosensor of claim 27 wherein said first optical path is along a straight line and said second optical path comprises a closed recirculating path.

29. The biosensor of claim 28 wherein said closed path comprises plural straight paths defining a polygonal shape.

30. The biosensor of claim 24 wherein said closed path lies along a circle.

31. The biosensor of claim 16 wherein said first biological entity comprises a first RNA strand and said second biological entity comprises a second RNA strand that is complementary to said first RNA strand.

* * * * *